United States Patent [19]
Chesterfield et al.

[11] Patent Number: 5,250,247
[45] Date of Patent: * Oct. 5, 1993

[54] METHOD AND APPARATUS FOR HEAT TIPPING SUTURES

[75] Inventors: Michael P. Chesterfield, Norwalk; Stanley J. Malinowski, Ridgefield; George R. Proto, West Haven, all of Conn.

[73] Assignee: United States Surgical Corporation, Norwalk, Conn.

[*] Notice: The portion of the term of this patent subsequent to Oct. 20, 2009 has been disclaimed.

[21] Appl. No.: 717,373

[22] Filed: Jun. 19, 1991

Related U.S. Application Data

[63] Continuation of Ser. No. 436,439, Nov. 14, 1989, Pat. No. 5,156,788.

[51] Int. Cl.⁵ .............................................. B29C 91/02
[52] U.S. Cl. ................................. 264/157; 264/291; 264/342 R; 264/346; 425/302.1; 425/446; 606/231
[58] Field of Search ........ 264/157, 291, 234, 342 RE, 264/342 R, 346; 425/446; 302.1; 604/905; 606/231, 228

[56] References Cited

U.S. PATENT DOCUMENTS

| | | |
|---|---|---|
| 1,665,216 | 4/1928 | Morton et al. |
| 2,280,603 | 7/1939 | Plambeck . |
| 2,296,394 | 9/1942 | Meloon . |
| 2,578,889 | 12/1951 | Kennedy . |
| 2,615,784 | 10/1952 | McClellan .................... 264/342 RE |
| 2,836,181 | 5/1958 | Tapp ..................... 264/324 |
| 2,847,703 | 8/1958 | Schrenk et al. ..................... 264/167 |
| 2,975,744 | 3/1961 | Smith . |
| 2,990,575 | 7/1961 | Gibbins et al. . |
| 3,020,120 | 2/1962 | Loliger ................................. 264/234 |
| 3,254,145 | 5/1966 | Tanguay . |
| 3,422,181 | 1/1969 | Chergwin, Jr. . |
| 3,491,418 | 1/1970 | Nicita et al. .......................... 28/71.3 |
| 3,493,646 | 2/1970 | Larkin et al. ................. 264/342 RE |
| 3,531,561 | 9/1970 | Trehu . |
| 3,574,804 | 4/1971 | Joonase . |
| 3,651,204 | 3/1972 | Nichols et al. . |
| 3,769,396 | 10/1973 | Espinosa . |
| 3,839,524 | 10/1974 | Adams et al. . |
| 3,875,946 | 4/1975 | Duncan . |
| 3,926,194 | 12/1975 | Greenberg et al. .................. 128/339 |
| 3,980,177 | 9/1976 | McGregor ....................... 128/335.5 |
| 4,443,215 | 4/1984 | Smith . |
| 4,832,025 | 5/1989 | Coates .............. 128/335.5 |
| 5,007,922 | 4/1991 | Chen et al. .................... 606/228 |
| 5,102,418 | 4/1992 | Granger et al. .................. 427/255.6 |

FOREIGN PATENT DOCUMENTS 2361119 4/1977 France .
1588031 4/1981 United Kingdom .

*Primary Examiner*—Jeffery Thurlow

[57] ABSTRACT

A heat tipping method and apparatus for surgical sutures to facilitate inserting the sutures into the barrel ends of surgical needles. The method comprises tensioning the suture, heating a portion of the suture to be heat tipped by blowing a current of hot air across the portion of the suture, and releasing the tension and cutting the portion of the suture to create heat tipped ends. The apparatus comprises a cylindrical drum around which the suture is wound, a concave channel in the drum for delimiting a portion of the suture to be heated, and hot air blowers for heating the delimited portions of the suture to a heat tipping temperature.

30 Claims, 6 Drawing Sheets

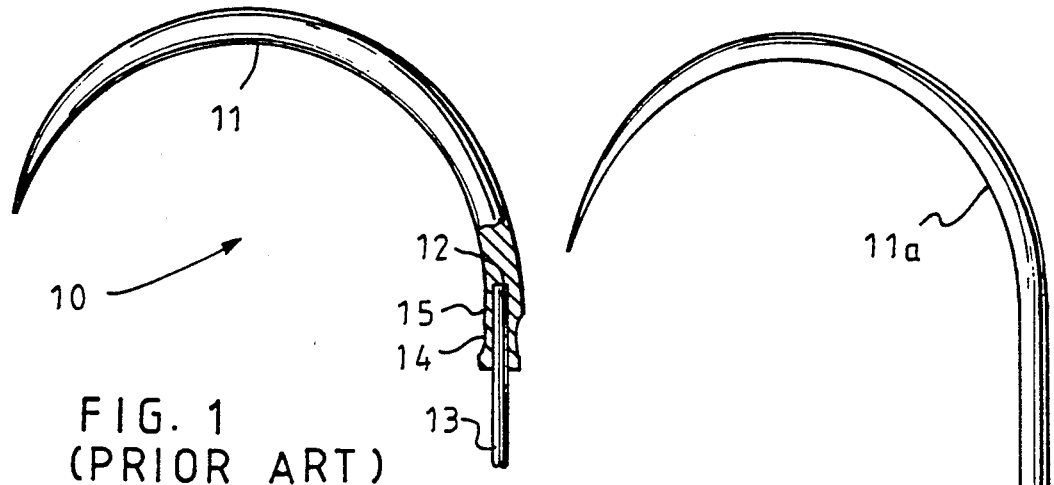
FIG. 1 (PRIOR ART)
FIG. 1a (PRIOR ART)
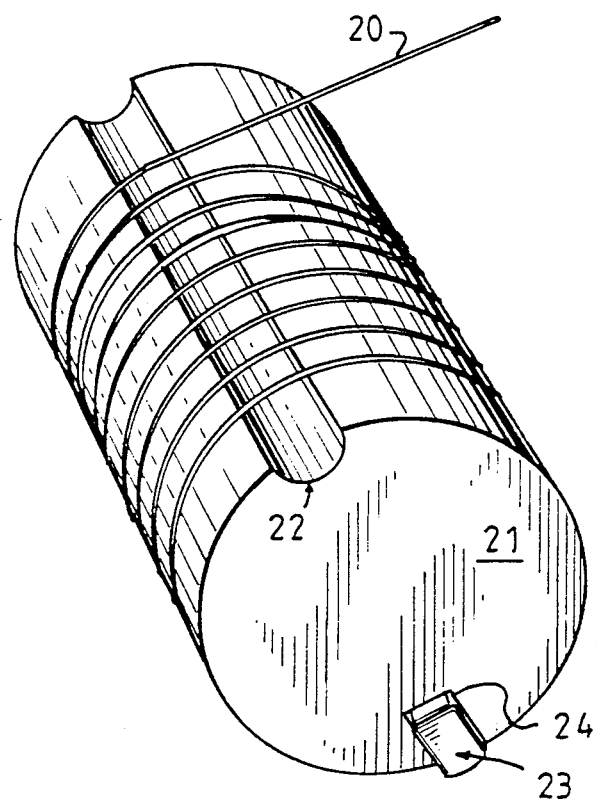
FIG. 2

METHOD AND APPARATUS FOR HEAT TIPPING SUTURES

This is a continuation of copending application Ser. No. 07/436,439 filed Nov. 14, 1989, U.S. Pat. No. 5,156,788 issued Oct. 20, 1992.

BACKGROUND OF THE INVENTION

1. Field of the Invention

This invention relates to surgical sutures and in particular to a surgical suture with a treated end for insertion into a surgical needle, and a treatment method therefor.

2. Background of the Art

Surgeons often use needles with attached sutures in surgical operations. A typical suture-needle combination is shown in FIG. 1. Generally, such needle suture combinations comprise a non-eyed needle with a cylindrical hole in a barrel shaped rear end for receiving a suture, and a suture with a treated end which is received into the hole. Provided with a needle suture combination, operating room personnel need not waste time trying to thread an eyed needle with a suture. After using the needle-suture combination to close a wound the surgeon may detach the needle either by cutting the suture or by pulling on the needle with sufficient force to detach the needle from the suture.

In making suture needle combinations, whether the needles be eyed or non-eyed, it is generally necessary to treat the tip of the suture in some manner in order to make it easier to insert the tip into the barrel end of the needle. Braided or woven sutures especially have a tendency to "broom" or flare out at the ends. The purpose of the treatment is to stiffen the tip of the suture, as, for example, the end of a sewing thread is wetted and twisted so that it may be inserted into the eye of a sewing needle.

With regard to surgical sutures, this "tipping" process generally has been accomplished by coating and/or soaking the end of the suture with a solution of a resinous tipping solution. One such solution is Mariotte mixture, which comprises a solution of polyamide resin in isopropyl alcohol and water. Another such solution is Gould mixture, which comprises a solution of polyamide resin in methanol.

Generally a suture to be tipped is first placed under tension to reduce slack so that it may be maintained in a predetermined position on a drum or other suture holding device. Optionally, the tension may be such as to reduce the diameter of the suture. The suture is then dipped into the tipping solution and allowed to dry while under tension. The sutures are then warmed in a drying oven at about 225° F. for about 10 minutes to dry the sutures. After drying the sutures can be cut and released from tension. The process results in a tipped end on each side of a cut. In cases where tension has optionally been employed to reduce the suture diameter, release of said tension will allow the suture to expand to its original diameter except at the tipped end portion. This can facilitate insertion of the end into a needle. A method for making a needle suture combination wherein the suture end has been treated with resin solutions is described in U.S. Pat. Nos. 3,980,177 and 3,890,975.

Although dipped sutures prepared in accordance with the above procedures have been used successfully, there are several drawbacks with the use of tipping solutions. The main problems are those of consistency and controllability. Non-uniform solvent evaporation, caused by variations in oven temperature and heating time, result in uneven diameter reduction and inconsistency of tipping. Furthermore, the dried residue of polymer left after evaporation can flake off or develop cracks.

A further drawback in these known procedures is that the suture is permanently altered. After the suture has been inserted into a needle there is no need for it to be stiffened. A limp suture will lay in the position in which the surgeon leaves it, whereas a stiff suture can interfere with the suturing operation. Nevertheless, a suture tipped by the prior art solutions will always have a portion containing the stiff residue of included polymer resin.

Heating of certain filaments is known in the art. A method for heat setting of stretch oriented polyglycolic acid filaments is disclosed in U.S. Patent No. 3,422,181. This patent discloses a method for improving the strength retention and absorption rate of a polyglycolic acid filament to be used in a suture by subjecting the filament to dry heat at a relative humidity of not greater than 20% and at a temperature of between 50° C. and 190° C.

Another method which has been employed for treating sutures involves melt fusion, as described in U.S. Pat. No. 4,832,025, issued to Coates. The suture is heated to a temperature at least high enough to "melt fuse" a portion of the outer filaments of the suture. Such temperature is typically about 260° C. to 300° C. (500° F. to 572° F.). The suture stiffens upon cooling. Surface melting of the outer filaments has the effect of holding the filaments together when the suture is cut. It also causes stiffening of the suture which facilitates insertion of the suture end into the drilled hole of a needle. However, the melt fusion of suture has significant drawbacks.

Firstly, the melt fusion of filaments weakens the suture, whose tensile strength is degraded in proportion to the extent of melt fusion.

Secondly, melt fusion causes an irreversible change in the filaments which results in permanent stiffening and permanent loss of tensile strength.

Thirdly, with the temperatures required for melt-fusion an inconveniently short heating cycle is required. For example, for a size 3/0 silicone coated polyester suture heated to between 260° C. to 300° C. in a 4 mm. diameter heating tunnel, the heating time is no more than about 3 seconds. Short heating times allow for more inconsistency and variation in the results of the tipping process than longer heating times.

What is needed is a method for heat tipping sutures which facilitates reversible stiffening of the suture without loss of tensile strength.

SUMMARY OF THE INVENTION

A method is disclosed for heat tipping sutures which is fully reversible and which causes substantially no loss of tensile strength. Heat tipping cycle times associated with the method of the present invention are of such duration to bring about evenness and consistency of results. The heat tipping method provided herein comprises delimiting a portion of the suture to be heat tipped, and heating the delimited portion of the suture to a heat tipping temperature and maintaining said temperature for a period of time, the heat tipping temperature being such as to cause the portion of the suture to be reversely stiffened upon cooling.

In a preferred form, a predetermined portion of the suture is selected. The selected portion is heated to a predetermined temperature sufficient to cause the portion to be reversibly stiffened when the heat is maintained for a predetermined period of time and the portion is then permitted to be cooled. In the preferred embodiment the invention contemplates permitting the delimited portion of the suture to cool passively, i.e. by contact with the surrounding air. However, it is with the scope of the invention to permit the delimited portion of the suture to cool actively, i.e. by blowing cool air thereby.

The method can additionally comprise winding the suture around a drum wherein the drum has a longitudinal concave channel or depression for delimiting a portion of the suture to be heated and a means for selectively adjusting the effective circumference of the drum relative to the suture.

The means for adjusting the circumference of the drum comprises a bar mounted within a longitudinal notch in the surface of the drum, the bar being radially movable between a position in which said bar extends a relatively further distance beyond the circumferential surface of the drum, and a position in which said bar extends a lesser distance or not at all beyond the circumferential surface of the drum. The bar is preferably spring mounted within a notch in the drum and resiliently biased to the first extending position.

Before heating the suture, tension can be applied to the suture by said means for adjusting the circumference of the drum.

The preferred tipping temperature is from about 300° F. to about 320° F., and heating is preferably accomplished by blowing a current of heated air across the suture. Blowing a stream of relatively cool air across the undelimited portion of the suture prevents the undelimited portion from being heated. The period of heating time optimally is determined in accordance with the diameter of the suture. The heat tipping method of the present invention can additionally comprise cutting the heated portion of the suture.

Also provided herein is an apparatus for heat tipping a suture, the apparatus comprising a cylindrical drum, means associated with said drum for delimiting a portion of the suture to be heat tipped, and means for heating the delimited portion of the suture to a heat tipping temperature. The means associated with said drum for delimiting a portion of the suture to be heat tipped comprises a concave channel or groove which extends longitudinally parallel to the axis of the drum. The means for heating the delimited portion of the suture to a heat tipping temperature preferably comprises an elongated hot air outlet for blowing air at a heat tipping temperature across the delimited portions of the suture.

The apparatus can additionally comprise means for applying tension to the suture, a means for cutting the heated portion of the suture to divide said portion into two heat tipped ends comprising a knife which is transversely movable across the heat tipped portion of the suture, and a means to prevent the non-delimited portion of the suture from being heat tipped comprising at least one row of cool air outlets for blowing relatively cool air across the non-delimited portion of the suture. The cylindrical drum optimally has a means for adjusting the drum circumference relative to suture which comprises a bar mounted within a longitudinal notch in surface of the drum, and the bar being radially movable between a position in which the bar extends a relatively further distance beyond the circumferential surface of the drum, and position in which the bar extends a relatively lesser distance or not at all beyond the circumferential surface of said drum. The bar is resiliently mounted, optimally by means of a spring.

BRIEF DESCRIPTION OF THE DRAWINGS

FIG. 1 illustrates a prior art needle-suture combination with a non-eyed needle;

FIG. 1a illustrates a prior art needle-suture combination with an eyed needle;

FIG. 2 is a perspective view of suture wound around a heat tipping apparatus constructed according to the present invention;

DETAILED DESCRIPTION OF THE INVENTION

Figure 3:
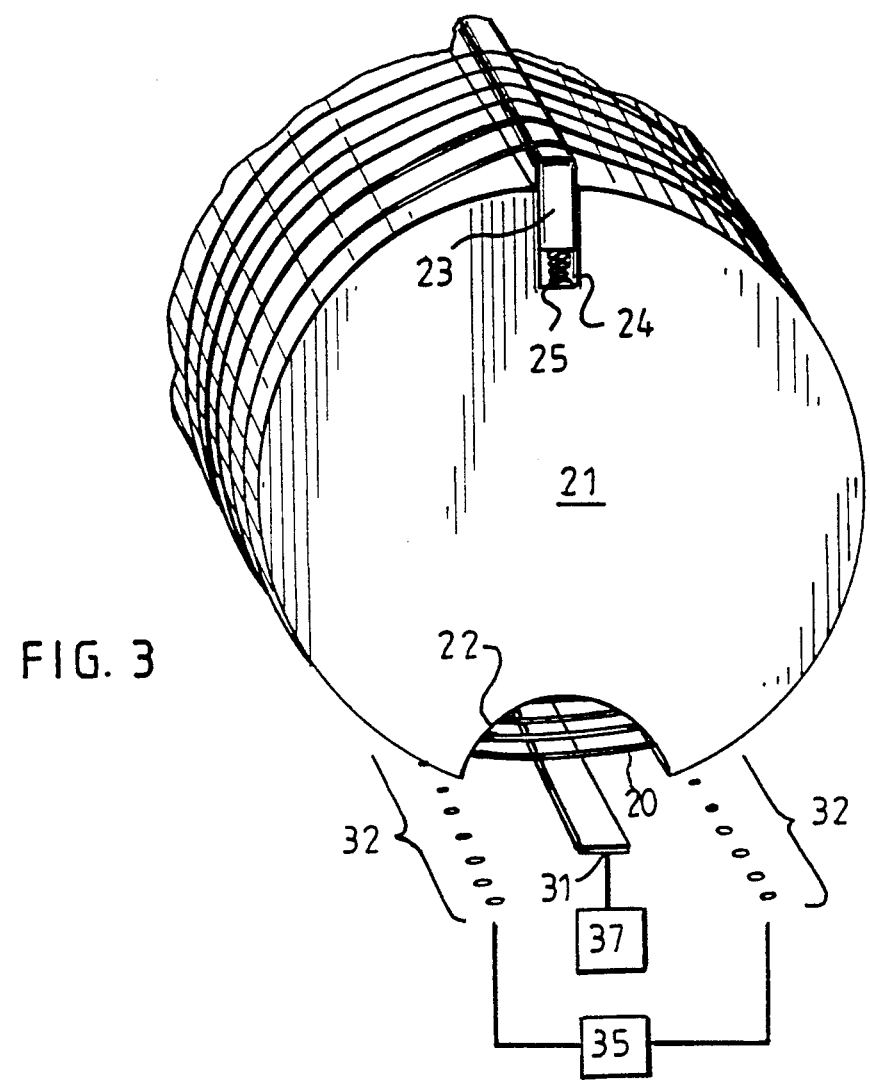
FIG. 3 illustrates the heat tipping drum positioned for the heat tipping procedure.

FIG. 1 illustrates a typical needle-suture combination 10 of the prior art. Needle 11 has a barrel shaped end 15 with a cylindrical hole 12 for receiving the end of suture 13. Once the suture is inserted a crimp 14 is put into the barrel to retain the suture. A needle-suture combination and methods and instrumentation for making such combination are disclosed in U.S. Pat. No. 3,980,177.

FIG. 1a illustrates a prior art eyed needle and suture combination. Needle 11a contains eye 16 through which suture 13a is threaded.

The heat tipping method of the present invention produces a suture which is reversibly stiffened. The heat tipped suture is stiff enough to be inserted into the barrel or eye of a surgical needle without brooming, but simple manipulation, such as bending and unbending the suture for example by drawing the fingers along the suture, will restore the flexibility and normal limpness of the suture as well as the original diameter if the diameter had been reduced by tensioning. This characteristic, i.e. reversible stiffening, is highly advantageous since there are no unwanted after effects from the tipping process such as residual stiffness or polymer residue, and it is not achieved by the prior art processes which fuse the surface filaments or glue them together with polymer resins.

Referring to FIGS. 2 and 3, a preferred method is disclosed for heat tipping sutures. The first step of the preferred heat tipping method of the present invention is to wind the suture around a cylindrical drum, preferably under tension so that there is no loose slack. Optionally, greater tension may be applied to reduce the suture diameter.

Suture 20 is wound around cylindrical drum 21. The drum is preferably constructed from metal, e.g., stainless steel, although other materials of construction, such as plastics, may be employed. The circumference of the drum may be chosen in accordance with the intended length of the individual sutures after cutting. Means for winding sutures under tension are conventional in the art.

Drum 21 has a concave channel or groove 22 which extends longitudinally along the surface of the drum 21 in an orientation parallel to the axis of the drum 21 and transverse to the orientation of the suture 20. The concave channel 22 provides a means for delimiting the portion or section of the suture to be heat tipped. As can be seen from FIGS. 2 and 3, the sutures 20 are stretched transversely across the mouth of the concave channel 22. The delimited portion of the suture is exposed for heating. The undelimited portion is held in close contact with the cylindrical drum 21, which is preferably made of thermally conductive metal and which therefore provides some protection of the non-delimited portion of suture 20 from heating by conducting heat away from said undelimited portion. Different widths of concave channel 22 will result in different lengths of tipped portions of the suture.

Drum 21 optionally comprises a means for varying the effective circumferential distance of drum relative to the suture. Changing the effective circumference of the drum provides a means for applying tension to the suture or reducing tension.

Referring to FIG. 3, the circumference adjusting device is preferably an elongated member or bar 23 which is mounted within a longitudinally extending notch 24 in the surface of drum 21. The bar 23 is movable radially between a position wherein the bar extends a relatively further distance beyond the surface of the drum (thereby presenting an effectively larger drum circumference to the suture and increasing suture tension) and a position wherein the bar extends a relatively lesser distance, or not at all, beyond the surface of the drum. In the last mentioned position, the bar presents an effectively smaller drum circumference to the suture and lessening suture tension.

After the suture has been wound around the drum as shown, the drum is positioned in a heat treating apparatus as diagrammed in FIG. 3. The drum 21 is mounted above an elongated heating outlet 31 supplied by a source of hot air 37 shown schematically in FIG. 3. Thus the portions of the sutures 20 to be heat tipped are arrayed in alignment over the heating outlet 31. On each side of the heating outlet 31 there is a parallelly extending line of cool air outlets 32. Heat tipping is optimally accomplished by blowing hot air from outlet 31 across the sutures 20. For this reason, the depth of channel 22 should be sufficient to accommodate adequate flow of the heated air past the delimited portions of the suture.

A source of cool air 35 shown schematically in FIG. 3 communicates with cool air from outlets 32 to provide a wall of cool air which protects the remaining portions of the sutures from inadvertent heating. The heat tipping process is optimally accomplished by providing a flow of hot air at a heat tipping temperature, which is defined as that temperature which causes a suture to be reversibly stiffened upon cooling to ambient or room temperature. Heat tipping is delimited by variables of temperature of air flow, duration of heating time, and suture diameter. A larger suture diameter requires a longer heating time, and a higher heating temperature requires a shorter heating time. The heat tipping temperature is at least high enough to cause some alteration in either the macroscopic structure or the molecular structure of the suture material, but it should not be so high as to cause melting or deterioration of the suture. The optimum heat tipping temperature range is from about 300° F. to about 320° F. Of the three parameters of heat tipping—temperature, time, and suture diameter—it is best to hold temperature constant. Heat tipping is optimally done at 300° F. to 320° F. for all suture diameters with an adjustment of heating time in accordance with suture diameter. Temperatures lower than about 295° F. produce no heat tipping, or require long periods of heating, whereas temperatures above about 330° F. may cause structural damage to the suture, or are associated with heating times which are too short to control easily.

Table I below sets forth a tabulation of heating times for various size sutures at the preferred heat tipping temperature of about 320° F. As can be seen from Table I, the heating times range from 12 to 16 seconds for size 5/0 sutures, to about 60 to 65 seconds for size 2 sutures These heating times allow the heat to transfer through the suture evenly and without localized inconsistencies caused by hot spots.

TABLE I

Copolymer of Glycolide and Lactide Type Suture
Heat Tipping Temperature = 320° F.

| Suture Size | Heating Time (seconds) |
| --- | --- |
| 2 | 60–65 |
| 1 | 50–55 |
| 1/0 | 42–46 |
| 2/0 | 25–30 |
| 3/0 | 22–28 |
| 4/0 | 14–18 |
| 5/0 | 12–16 |

Figure 4:
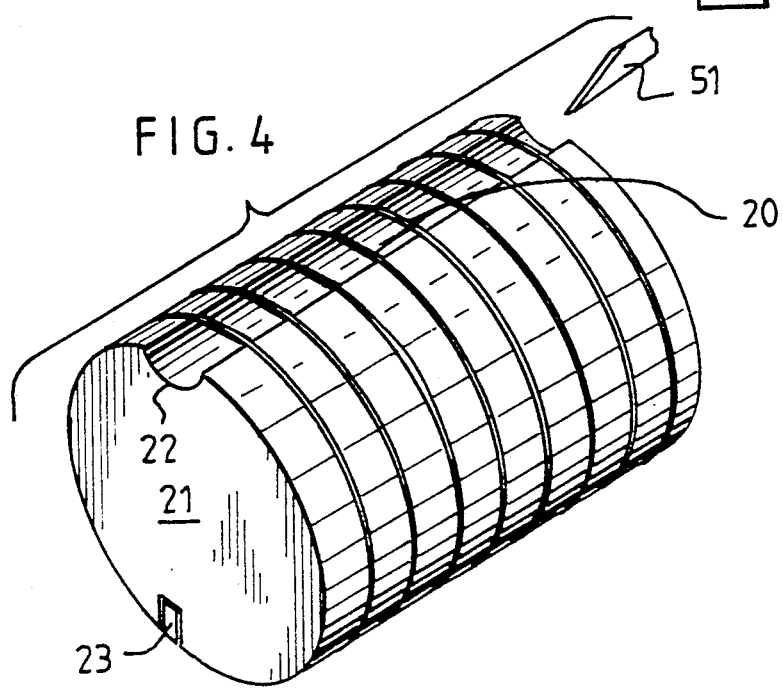
FIG. 4 illustrates the cutting operation.
Figure 5A:
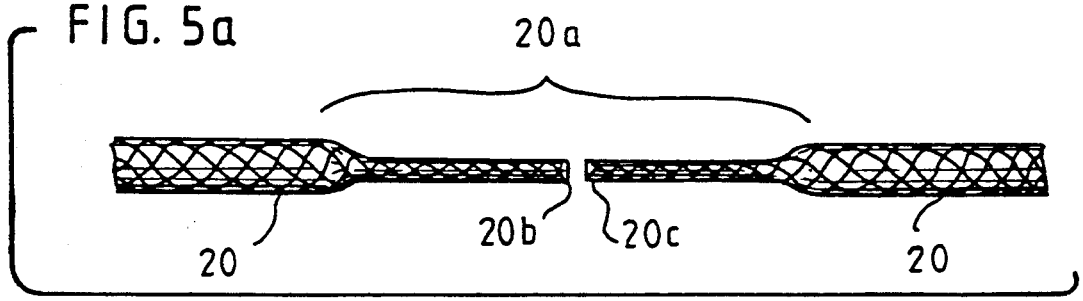
FIGS. 5a and 5b are side views of a heat tipped suture with and without diameter reduction, respectively.
Figure 5B:
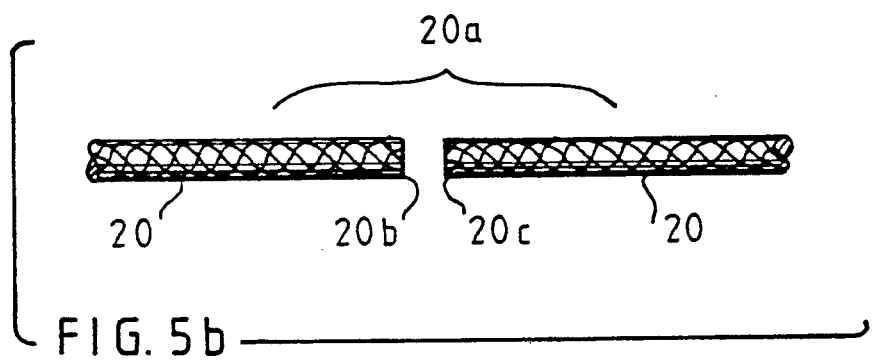

Referring to FIGS. 4, 5a and 5b, after the heating is completed the suture 20 (90% glycolide/10% lactide) is allowed to cool to ambient or room temperature and the diameter modifier 23 is depressed to reduce tension. A knife 51 is drawn laterally across the heat tipped portion of the sutures 20a thereby cutting them and creating two heat tipped ends, 20b and 20c, at each cut. In cases where the suture diameter has been reduced through tensioning, it should be noted that when the tension is released the suture will expand to its original diameter except at the heat tipped portion 20a, which retains the smaller diameter of the tensioned suture, as shown in FIG. 5a. When the suture has not been tensioned so as to reduce its diameter the heat tipping process of the present invention will nevertheless facilitate insertion of the tipped end into a needle by stiffening the end and by preventing brooming of the braided filaments, as illustrated in FIG. 5b.

The heat tipped portion 20a provided in accordance with the present invention is stiff and is easily insertable into the barrel end of a surgical needle. Braided sutures which are heat tipped will not "broom" or expand. The heat tipped portion may be restored to substantially its original flexibility and limpness by manipulating it. e.g. running it through one's fingers while bending and curling it.

Heat tipping according to the present invention may be performed on a variety of suture materials such as, but not limited to, polymers and copolymers of glycolide and lactide, polydioxanone, collagen, silk, nylon, dacron, cotton, linen, etc., preferably braided.

Figure 6:
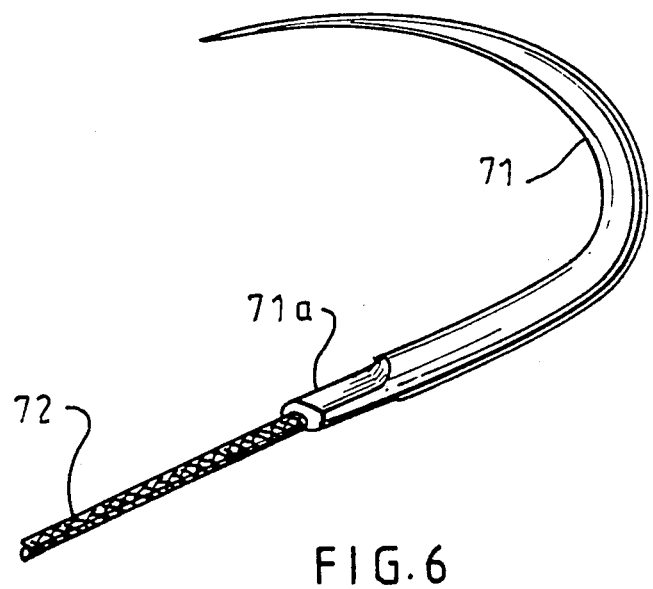
FIG. 6 is a perspective view of a combination of a needle and a heat tipped suture.

FIG. 6 illustrates a needle suture combination employing a suture prepared in accordance with the present invention. Needle 71 has a barrel end 71a into which heat tipped braided suture 72 is inserted. The suture is fixed by crimping or swaging the barrel end as illustrated.

Figure 7A:
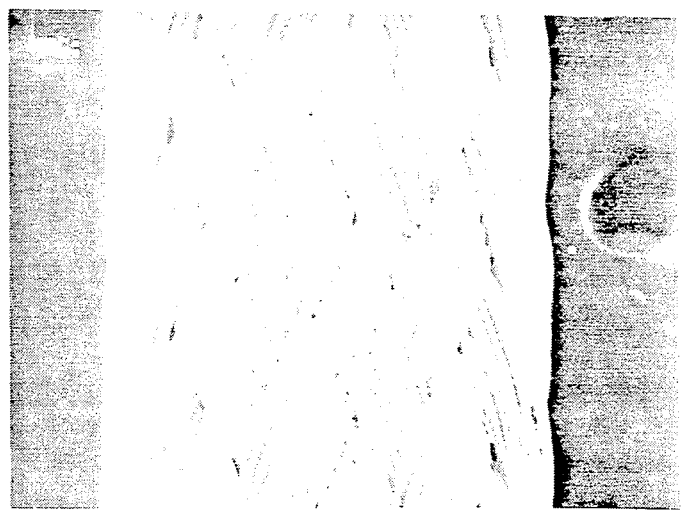
FIGS. 7a and 7b are photomicrographs illustrating the non-heat tipped control portion of the surface of a braided suture at magnifications of 100 and 1000, respectively.
Figure 7B:
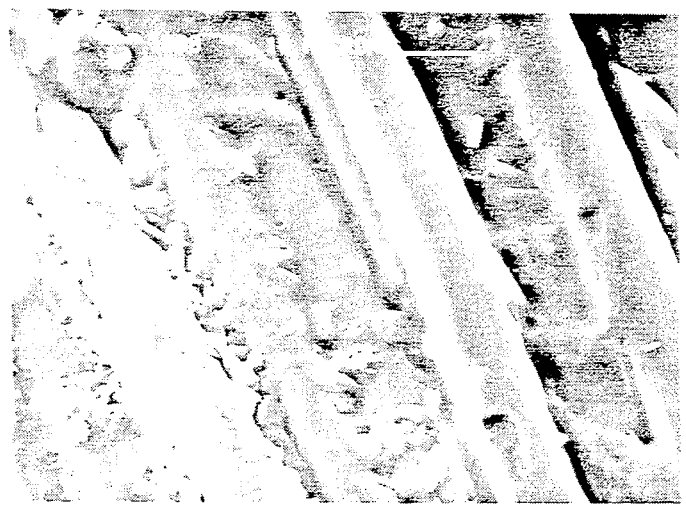

FIGS. 7a and 7b illustrate a control portion of a coated synthetic absorbable suture.

Figure 8A:
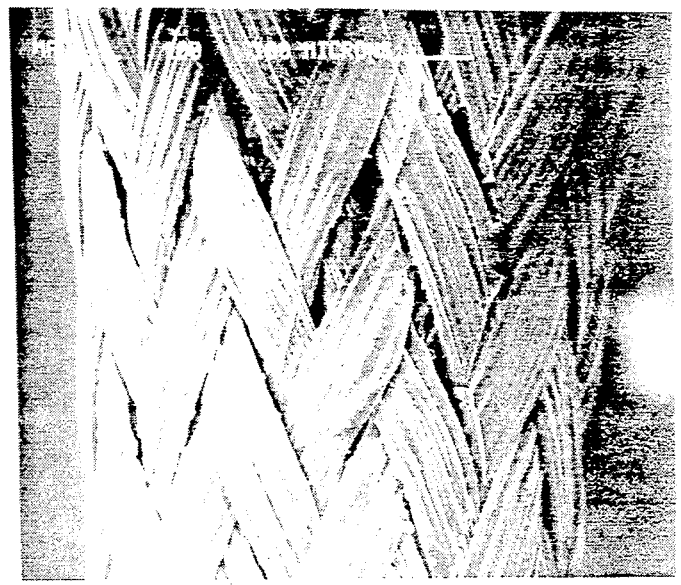
FIGS. 8a and 8b are photomicrographs illustrating the surface portion of a braided suture which has been heat tipped in accordance with the present invention, at magnification of 100 and 1000, respectively.
Figure 8B:
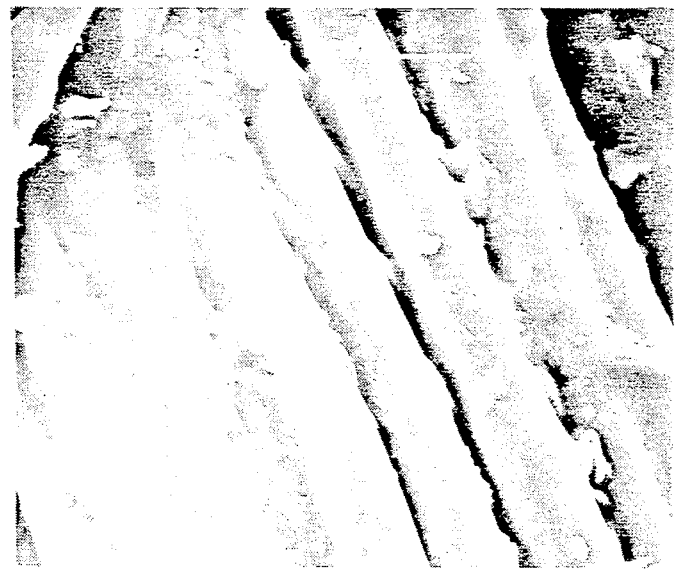

FIGS. 8a and 8b show the same suture in the heat tipped region. As is apparent from a comparison of the control region and the heat tipped region, there is no evidence of fusing or melting of the filaments by the heat tipping process of the present invention.

Figure 9A:
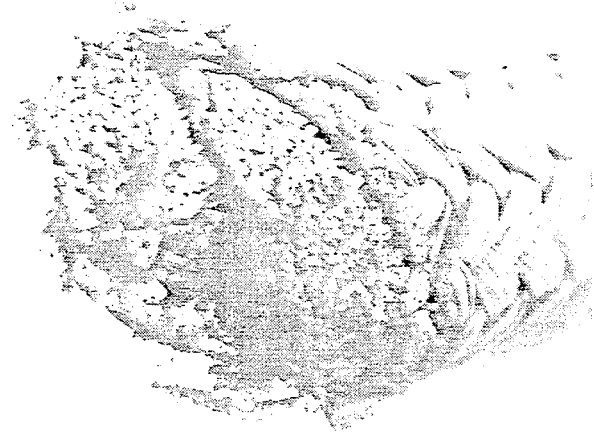
FIGS. 9a and 9b are photomicrographs illustrating the cut end of a portion of a suture which has been heat tipped in accordance with the present invention, at magnifications of 75 and 1000, respectively.
Figure 9B:

FIGS. 9a and 9b show the cut end of the heat tipped region of a suture. As can be seen from the photomicrographs the heat tipping process of the present invention effectively eliminates fraying or brooming at the cut end of the suture, thereby permitting insertion of the cut end into barrel end of a surgical needle, but without permanently rigidifying the heat tipped region of the suture.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for heat treating a surgical suture comprising:
   a) delimiting a portion of the suture to be heat treated; and,
   b) heating the delimited portion of the suture to a temperature which is maintained for a period of time sufficient to cause the delimited portion of the suture to become stiffened upon cooling.

2. The method of claim 1 wherein the delimiting step comprises winding the suture around a drum.

3. The method of claim 1 wherein the drum includes a longitudinal concave channel for delimiting a portion of the suture to be heated.

4. The method of claim 1 wherein the drum comprises means for selectively adjusting the effective circumference of the drum relative to the suture.

5. The method of claim 4 wherein the means for selectively adjusting the effective circumference of the drum comprises an elongated member mounted within a longitudinal notch in the surface of the drum, the elongated member being radially movable between a position in which the elongated member extends a relatively greater distance beyond the circumferential surface of the drum, and a position in which the elongated member extends a lesser distance or not at all beyond the circumferential surface of the drum.

6. The method of claim 5 wherein the elongated member is spring mounted within a notch in the drum and resiliently biased to the further-extending position.

7. The method of claim 4 further comprising applying a tensioning force to at least the delimited portion of the suture before heating.

8. The method of claim 7 wherein the tension is applied by the means for adjusting the effective circumference of the drum.

9. The method of claim 1 wherein heating a portion of the suture comprises blowing a current of heated air across at least the delimited portion of the suture.

10. The method of claim 1 further comprising blowing a stream of relatively cool air across the non-delimited portion of the suture to prevent or inhibit the non-delimited portion of the suture from being heated.

11. The method of claim 1 wherein the period of time of heating is determined in accordance with the diameter of the suture.

12. The method of claim 1 additionally comprising cutting the heated portion of said suture.

13. The method of claim 12 wherein the cutting step forms a suture end portion.

14. The method of claim 1 wherein said delimited suture portion comprises a suture end portion.

15. The method of claim 1 wherein the period of time of heating is determined in accordance with the size of the suture.

16. The method of claim 1 wherein the heating step comprises heating the delimited portion of the suture for a period of time determined in accordance with the suture size as follows:

| Suture Size | Heating Time (sec.) |
| --- | --- |
| 2 | 60-65 |
| 1 | 50-55 |
| 1/0 | 42-46 |
| 2/0 | 25-30 |
| 3/0 | 22-28 |
| 4/0 | 14-18 |
| 5/0 | 12-16. |

17. The method of claim 1 wherein the heating step comprises exposing the delimited portion of the suture to a temperature of about 320° F. for a period of time determined in accordance with suture size as follows:

| Suture Size | Heating Time (sec.) |
| --- | --- |
| 2 | 60-65 |
| 1 | 50-55 |
| 1/0 | 42-46 |
| 2/0 | 25-30 |
| 3/0 | 22-28 |
| 4/0 | 14-18 |
| 5/0 | 12-16. |

18. The method of claim 1 wherein the suture is a multifilament braided suture.

19. The method of claim 1 wherein the suture is fabricated from a material selected from the group consisting of polyglycolide, polylactide, copolymers of glycolide and lactide, polydioxanone, collagen, silk, nylon, dacron, cotton and linen.

20. A method for heat treating a delimited portion of a surgical suture comprising:
   a) selecting a predetermined portion of the suture;
   b) heating the delimited portion of the suture to a predetermined temperature sufficient to cause the delimited portion of the suture to be reversibly stiffened when the heat is maintained for a predetermined period of time and the delimited portion of the suture is permitted to cool;
   c) maintaining the temperature for the predetermined period of time; and, d) permitting the delimited portion of the suture to be cooled.

21. In a method for producing a surgical suture having a reduced diameter end portion resulting from application of a suture diameter reducing tensioning force to at least a delimited portion of the suture, the improvement which comprises heating the delimited portion of the suture while the suture is in a helical configuration.

22. The method of claim 21 wherein the delimited portion of the suture is heated to a temperature of from about 300° F. to about 320° F.

23. The method of claim 21 wherein the suture is wrapped around a drum in a helical configuration.

24. The method of claim 21 wherein the delimited portion of the suture is severed following heating to provide two reduced diameter end portions.

25. An apparatus for producing a surgical suture having a reduced diameter end portion which comprises:
   a) a drum possessing means for delimiting a portion of suture wound upon the drum;
   b) means for applying a suture diameter-reducing tension to the delimited portion of the suture wound upon the drum; and,
   c) means for heating the delimited portion of suture wound upon the drum.

26. The apparatus of claim 25 wherein the drum is substantially cylindral and the means for delimiting a portion of suture wound upon the drum comprises a longitudinally extending channel defined upon the surface of the drum with the delimited portion of suture avoiding contact with the surface of the channel.

27. The apparatus of claim 26 wherein the means for heating the delimited portion of suture wound upon the drum provides a temperature of from about 300° F. to about 320° F.

28. The apparatus of claim 26 further comprising means for cutting the delimited portion of the suture wound upon the drum so as to provide two reduced diameter end portions.

29. The apparatus of claim 28 wherein the means for cutting the delimited portion of suture wound upon the drum is a knife.

30. The apparatus of claim 28 wherein the drum is substantially cylindrical and the means for delimiting a portion of suture wound upon the drum comprises a longitudinally extending channel defined upon the surface of the drum with the delimited portion of suture avoiding contact with the surface of the channel.

* * * * *